United States Patent [19]

Ouellette et al.

[11] Patent Number: 5,431,643

[45] Date of Patent: Jul. 11, 1995

[54] ABSORBENT ARTICLE HAVING A NONWOVEN TOPSHEET WITH FLUID IMPERVIOUS AREAS

[75] Inventors: William R. Ouellette, Cincinnati, Ohio; Teresa A. Vollmecke, W. Harrison, Ind.; Bruce W. Lavash, West Chester, Ohio

[73] Assignee: The Procter & Gamble Company, Cincinnati, Ohio

[21] Appl. No.: 111,097

[22] Filed: Aug. 24, 1993

Related U.S. Application Data

[63] Continuation-in-part of Ser. No. 862,383, Apr. 2, 1992, abandoned.

[51] Int. Cl.⁶ .......................... A61F 13/15; A61F 13/20
[52] U.S. Cl. .................. 604/385.1; 604/358; 604/366; 604/370; 604/378; 604/381
[58] Field of Search .............. 604/358, 365–366, 604/370–371, 378–380.1, 361–362

[56] References Cited

U.S. PATENT DOCUMENTS

| | | | |
|---|---|---|---|
| 2,536,631 | 1/1951 | Ely | 604/362 |
| 3,828,783 | 8/1974 | Kennette et al. | 604/366 |
| 3,879,942 | 4/1975 | Roberts et al. | 604/370 |
| 3,886,941 | 6/1975 | Duane et al. | 604/366 |
| 4,355,066 | 10/1982 | Newman | 604/366 |
| 4,397,644 | 8/1983 | Matthews et al. | 604/378 |
| 4,673,403 | 6/1987 | Lassen | 604/361 |
| 4,781,962 | 11/1988 | Zamarripa et al. | 604/382 |
| 5,219,341 | 6/1993 | Serbiak et al. | 604/361 |
| 5,328,450 | 7/1994 | Smith et al. | 604/366 |

FOREIGN PATENT DOCUMENTS

| | | |
|---|---|---|
| 0400694 | 5/1990 | European Pat. Off. |
| 2242348A | 2/1991 | United Kingdom. |
| WO91/10415 | 7/1991 | WIPO. |

*Primary Examiner*—Randall L. Green
*Assistant Examiner*—P. Zuttarelli
*Attorney, Agent, or Firm*—William Scott Andes; Kevin C. Johnson; E. Kelly Linman

[57] ABSTRACT

An absorbent article including a fluid pervious topsheet, a fluid impervious backsheet joined to the topsheet, and an absorbent core positioned between the topsheet and the backsheet. The topsheet includes a fluid pervious nonwoven material having a patterned network of fluid impervious areas deposited thereon. Bodily fluid deposited on the topsheet is transported through the fluid pervious nonwoven material portion of the topsheet, thereby wetting the nonwoven material while the fluid impervious areas remain dry. The dry fluid impervious areas contrast visually with the wetted nonwoven material portion of the topsheet. This structure provides a topsheet that is perceived as soft and fibrous prior to the discharge of bodily fluids thereon and clean and dry after bodily fluids have been deposited thereon.

20 Claims, 3 Drawing Sheets

ABSORBENT ARTICLE HAVING A NONWOVEN TOPSHEET WITH FLUID IMPERVIOUS AREAS

CROSS-REFERENCE TO RELATED APPLICATION

This application is a continuation-in-part of the application having U.S. Ser. No. 07/862,383, now abandoned filed Apr. 2, 1992 in the names of William R. Ouellette, Teresa A. Vollmecke, and Bruce W. Lavash.

FIELD OF THE INVENTION

The present invention relates to absorbent articles such as sanitary napkins, diapers, and incontinent articles, and the like, and more particularly, to such absorbent articles having a nonwoven topsheet with fluid impervious areas thereon.

BACKGROUND OF THE INVENTION

All manner and variety of absorbent articles configured for the absorption of bodily fluids are, of course, well known. Current types of absorbent articles include sanitary napkins, diapers, and incontinent articles.

A topsheet is the portion of an absorbent article which covers one face of the absorbent article which typically contacts the skin of the person using the absorptive devise. It has long been known in the disposable absorbent article art that it is extremely desirable to construct absorptive devices, such as disposable sanitary napkins, diapers, incontinent articles, and the like, with a topsheet providing a tactilely soft feel to the user prior to the discharge of bodily fluids thereon and also provide a clean and dry surface after the discharge of bodily fluids thereon.

U.S. Pat. No. 4,041,951 issued to Sanford on Aug. 16, 1977 and hereby incorporated herein by reference, discloses a preferred disposable diaper structure comprising a substantially planar, moisture absorbent layer disposed between a soft topsheet and a moisture-resistant backing sheet. The fibrous nonwoven topsheet preferably comprises an integral structure containing a multiplicity of depressed areas which intimately contact the uppermost surface of a substantially planar, moisture absorbent layer. The nondepressed areas of the topsheet contact the wearer's skin in-use. This fibrous nonwoven topsheet is particularly well suited for the user who prefers the soft feel of a nonwoven topsheet prior to the discharge of bodily fluids thereon. However, this fibrous nonwoven topsheet does not provide a visually clean and dry surface after bodily fluids, e.g., menses or blood, have been discharged thereon and have wetted the fibrous nonwoven topsheet.

U.S. Pat. No. 4,798,608 issued to Meyer et al. on Jan. 17, 1989 and hereby incorporated herein by reference, discloses an absorbent article having a hydrophobic transport layer. A nonwoven topsheet is superposed in facing relation with the absorbent body, and has an effective average pore size therein. A transport layer is located between the absorbent body and the topsheet which has an effective average pore size which is smaller than the pore size of the topsheet. This nonwoven structure will provide the user with a topsheet having a soft feel prior to the discharge of bodily fluids thereon. However, the nonwoven topsheet will not provide a visually clean and dry surface after bodily fluids have been discharged thereon and have wetted the nonwoven topsheet.

U.S. Pat. No. 4,780,352 issued to Palumbo on Oct. 25, 1988 and hereby incorporated herein by reference, discloses a perforated covering structure for absorbent hygienic-sanitary products. The perforated covering structure has an upper layer of nonwoven hydrophobic fibers, an intermediate layer of hydrophobic film and a lower layer of nonwoven hydrophobic fibers. This structure will be well suited for the user who prefers the soft feel of the nonwoven prior to the discharge of bodily fluids thereon. However, bodily fluids deposited on the covering structure will remain in the upper layer creating a visually unclean and wet surface for the user.

U.S. Pat. No. 4,342,314 issued to Radel et al. on Aug. 3, 1982 and hereby incorporated herein by reference, discloses a resilient plastic web exhibiting a fiber-like appearance and tactile impression. The web exhibits a fine scale three-dimensional microstructure comprising a regulated continuum of capillary networks, preferably of steadily decreasing size, originating in and extending from a first surface of the web and terminating in the form of apertures in a second surface of the web to promote rapid fluid transport from the first surface to the second surface. This apertured three-dimensional plastic web topsheet is particularly well suited for the user who prefers a clean and dry surface after the discharge of bodily fluids thereon. Although effective in the transfer of bodily fluids away from the wearer's skin, it has been learned that some users find it psychologically and/or physically undesirable to employ a material which is plastic in direct contact with their skin.

SUMMARY OF THE INVENTION

The present invention pertains, in a preferred embodiment, to an absorbent article having a fluid pervious topsheet, a fluid impervious backsheet joined to the topsheet, and an absorbent core positioned between the topsheet and the backsheet. The topsheet includes a fluid pervious nonwoven material having a first surface. The first surface of the nonwoven material has a patterned network of fluid impervious areas deposited thereon, such that bodily fluid deposited on the topsheet is transported through the fluid pervious nonwoven material thereby wetting the fluid pervious nonwoven material portion of the topsheet, while the fluid impervious areas remain dry and contrast visually with the fluid pervious nonwoven material.

Preferably, the topsheet is an apertured nonwoven material. More preferably, the first surface of the topsheet has from about 10 percent to about 70 percent of its area covered by the fluid impervious areas. In a preferred embodiment the fluid impervious areas are pigmented.

Preferably, the absorbent article includes an adhesive fastening means secured to the backsheet adapted to secure the absorbent article to an undergarment.

BRIEF DESCRIPTION OF THE DRAWINGS

While the specification concludes with claims particularly pointing out and distinctly claiming the subject matter of the present invention, it is believed that the present invention will be better understood from the following description in conjunction with the accompanying drawings, in which like reference numerals identify identical elements and wherein:

DETAILED DESCRIPTION OF THE PRESENT INVENTION

I. INTRODUCTION

Figure 1:
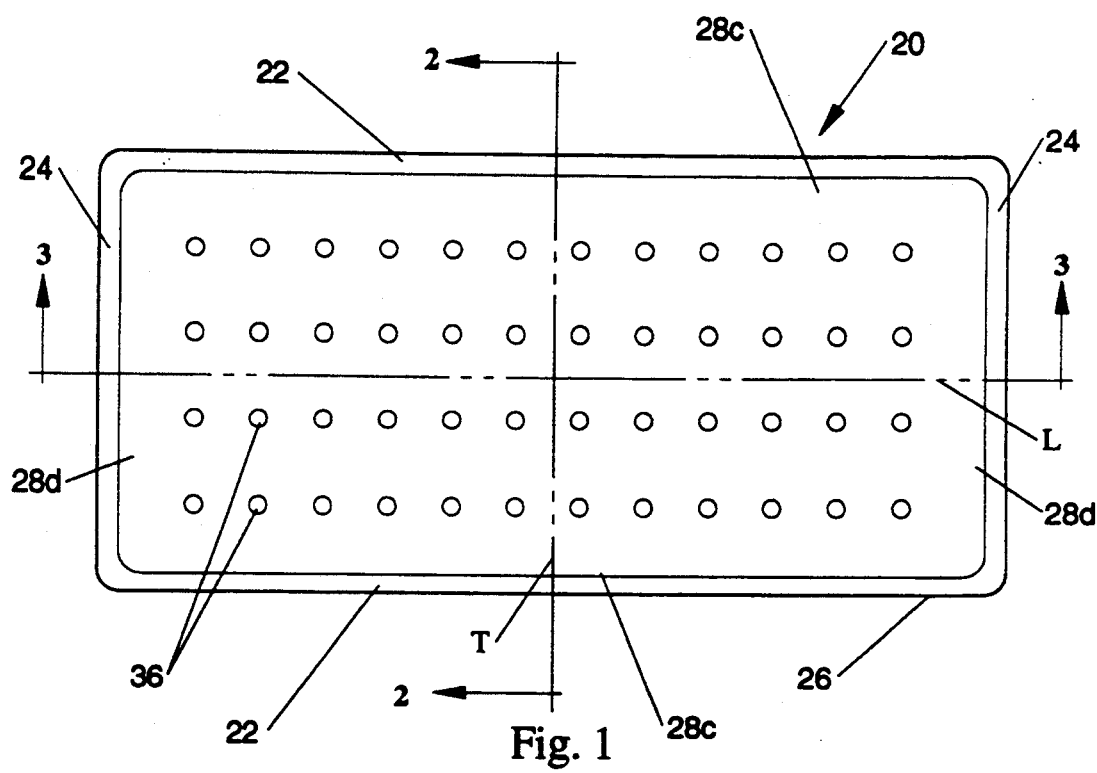
FIG. 1 is a simplified illustration of an absorbent article of the present invention.

While the present invention will be described in the context of providing a nonwoven web of material having fluid impervious areas thereon for use as a topsheet on a sanitary napkin, the present invention is in no way limited to such application. To the contrary, the present invention may be applied to great advantage in many absorbent articles such as diapers, incontinent articles, and the like.

The term "absorbent article", as used herein, refers to articles which absorb and contain body exudates. More specifically, the term refers to articles which are placed against or in proximity to the body of the wearer to absorb and contain the various exudates discharged from the body. The term "absorbent article" is intended to include sanitary napkins, diapers, incontinent articles, pantiliners, and other articles used to absorb body exudates. The term "disposable" refers to articles which are intended to be discarded after a single use and preferably recycled, composted, or otherwise disposed of in an environmentally compatible matter. (That is, they are not intended to be laundered or otherwise restored or reused as an absorbent article.) In the preferred embodiment illustrated, the absorbent article is a sanitary napkin designated 20.

The term "sanitary napkin", as used herein, refers to an article which is worn by females adjacent to the pudendal region that is intended to absorb and contain the various exudates which are discharged from the body (e.g., blood, menses, and urine). The present invention, however, is not limited to the particular types or configurations of absorbent articles shown in the drawings.

The sanitary napkin 20 has two surfaces, a first or wearer-contacting surface 20a and a second or garment contacting surface 20b. The sanitary napkin 20 is shown in FIG. 1 as viewed from its first or wearer-contacting surface 20a. The first or wearer-contacting surface 20a is intended to be worn adjacent to the body of the wearer. The second or garment contacting surface 20b of the sanitary napkin 20 (shown in FIG. 2) is on the opposite side and is intended to be placed adjacent to the wearer's undergarments when the sanitary napkin 20 is worn.

The sanitary napkin 20 has two centerlines, a longitudinal centerline "l" and a transverse centerline "t". The term "longitudinal", as used herein, refers to a line, axis or direction in the plane of the sanitary napkin 20 that is generally aligned with (e.g., approximately parallel to) a vertical plane which bisects a standing wearer into left and right body halves when the sanitary napkin 20 is worn. The terms "transverse" or "lateral", as used herein, are interchangeable, and refer to a line, axis or direction which lies within the plane of the sanitary napkin 20 that is generally perpendicular to the longitudinal direction. FIG. 1 shows that the sanitary napkin 20 also has two spaced apart longitudinal or side edges 22 and two spaced apart transverse or end edges (or "ends") 24, which together form the periphery 26 of the sanitary napkin 20.

The sanitary napkin 20 can be of any thickness, including relatively thick or relatively thin. The embodiment of sanitary napkin 20 shown in FIGS. 1–3 of the drawings is intended to be an example of a relatively thin sanitary napkin. It should be understood, however, when viewing these Figures the number of layers of material shown causes the sanitary napkin 20 to appear much thicker than it actually is. A "thin" sanitary napkin 20 preferably has a caliper of less than about 3 millimeters. The thin sanitary napkin 20 shown should also be preferably relatively flexible, so that it is comfortable for the wearer.

Figure 2:
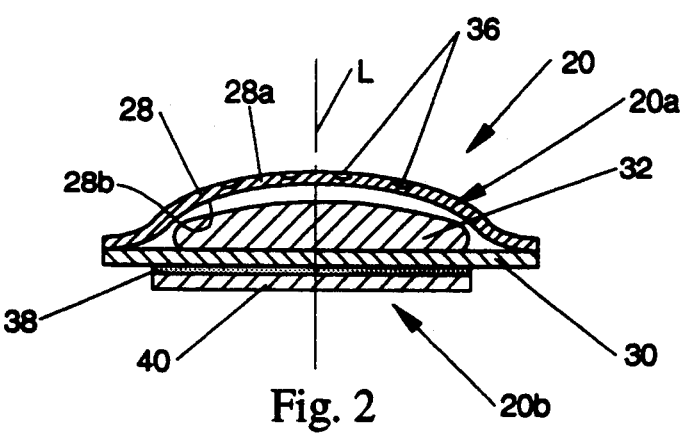
FIG. 2 is a cross-sectional view taken along section line 2—2 of FIG. 1.

FIG. 2 shows the individual components of the sanitary napkin. The sanitary napkin 20 of the present invention generally comprises at least three primary components. These include a liquid pervious topsheet 28, a liquid impervious backsheet (or "barrier means") 30, and an absorbent core 32. The absorbent core 32 is positioned between the topsheet 28 and the backsheet 30. The sanitary napkin 20 also has an adhesive fastening means 38 for attaching the sanitary napkin 20 to the undergarment of the wearer. Removable release liners 40 cover the adhesive fastening means 38 to keep the adhesive from sticking to a surface other than the crotch portion of the undergarment prior to use.

II. Individual Components of the Absorbent Article

The individual components of the sanitary napkin 20 will now be described in greater detail.

A. The Topsheet

The topsheet 28 is fluid pervious and when the sanitary napkin 20 is in use, the topsheet 28 is in close proximity to the skin of the user. The topsheet 28 is compliant, soft feeling, and nonirritating to the user's skin.

The topsheet 28 has two surfaces, including a first or wearer-contacting surface 28a, and a second, absorbent element or pad contacting surface 28b. The first or wearer-contacting surface 28a of the topsheet 28 generally forms at least a portion of the wearer-contacting surface 20a of the sanitary napkin 20. The topsheet 28 has two longitudinal edges 28c and two end edges 28d. (A similar numbering system will be used for other components of the sanitary napkin. That is, the side of the component facing the wearer's body will be designated by the number of the component and a reference letter "a". The side facing the wearer's undergarments will be designated by the number and the letter "b". The side and edges will be designated by the number and the component and the reference letters "c" and "d" respectively.)

Topsheet 28 may be preferably manufactured of a nonwoven material. A suitable nonwoven material may be selected from a wide range of materials such as natural fibers (e.g., wood or cotton fiber), synthetic fibers (e.g., polymeric fibers, such as polyester, polypropylene fibers, and polyethylene, or polyvinylalcohol, starch base resins, polyurethanes, cellulose esters, nylon and rayon fibers) or from a combination of natural and synthetic fibers.

Clearly, there are a number of manufacturing techniques which may be utilized to manufacture the nonwoven topsheet 28. For example, nonwoven topsheet 28 may be resin-bonded, needle punched, air-laid, wet-laid, spunbonded, carded, the latter including, thermally bonded, air-thru bonded, spunlaced, hydroapertured, and other apertured fabrics. A preferred nonwoven topsheet 28 comprises a thermally bonded carded polypropylene fabric.

One preferred nonwoven fabric comprises a carded thermally dot bonded polypropylene web. Another preferred nonwoven is a spunbonded thermally bonded polypropylene web. Still another preferred nonwoven fabric 28 is a carded polypropylene web which is embossed in accordance with the method described in U.S. Pat. No. 4,781,710 issued to Megison, et al. on Nov. 1, 1988 and hereby incorporated herein by reference. This nonwoven fabric 28 has diamond shaped embossed and thermally bonded areas. (The embossing need not extend into the underlying core, however.)

Figure 3:
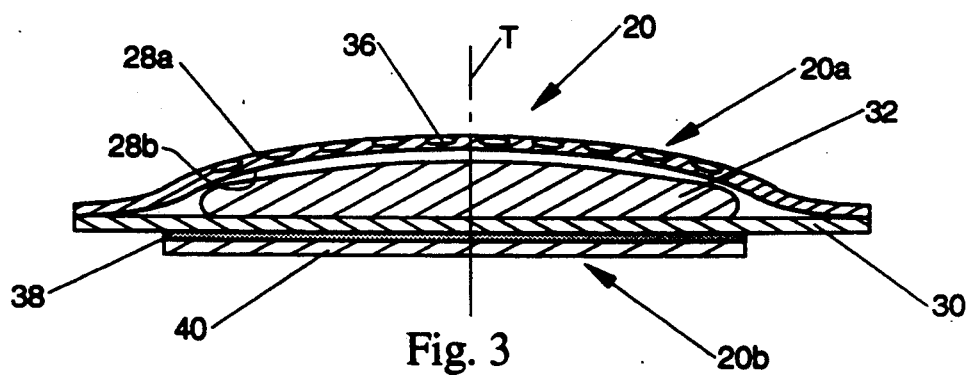
FIG. 3 is a cross-sectional view taken along section line 3—3 of FIG. 1.
Figure 6:
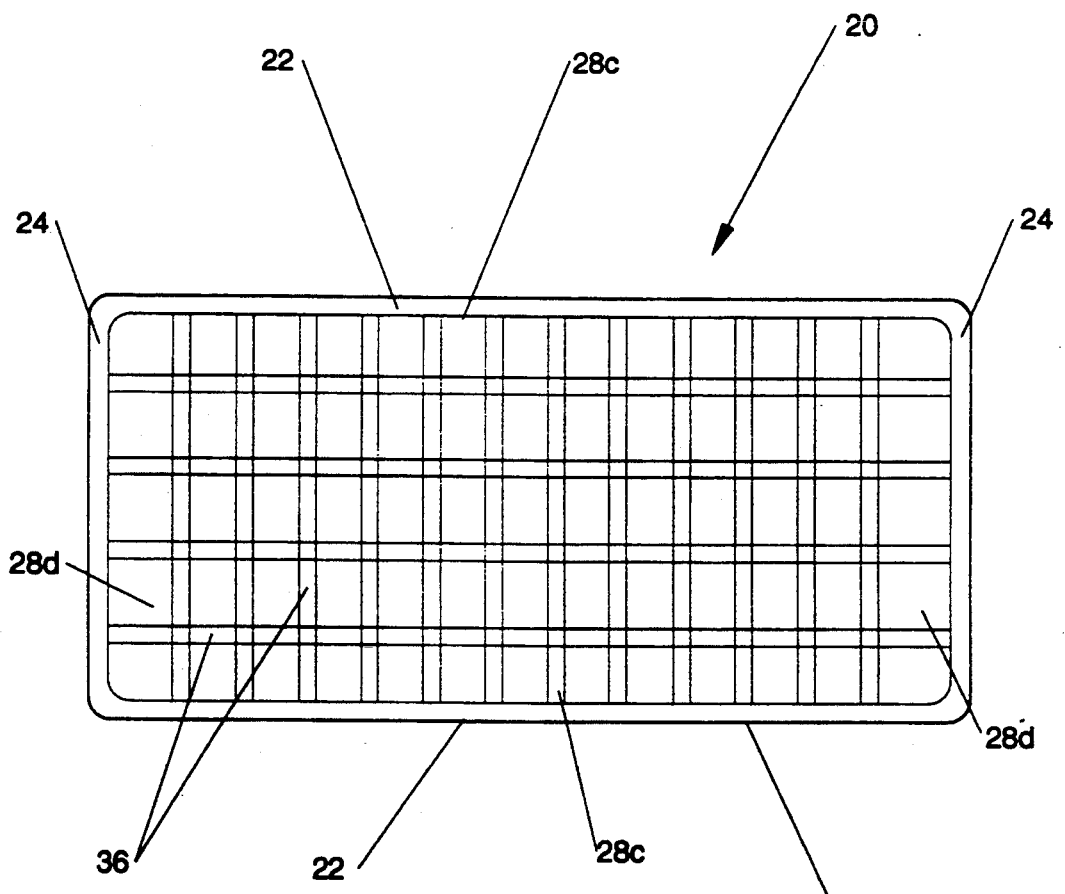
FIG. 6 is a simplified illustration of an absorbent article of the present invention.

FIGS. 1–3 show that the topsheet 28 is provided with a multiplicity of fluid impervious areas 36. The fluid impervious areas 36 as seen in FIGS. 1–3 are arranged in a discontinuous pattern on topsheet 28. Alternatively, the fluid impervious areas 36 can be arranged in a continuous pattern on topsheet 28, as seen in FIG. 6. Fluid impervious areas 36 are preferably made of ink. Other suitable materials which can be used for the fluid impervious areas 36 include, but are not limited to cellulose acetate, polyethylene, polypropylene or any other material compatible with the various processes that can be used. Preferably, the fluid impervious areas 36 will be pigmented such that they exhibit minimal or no visual contrast with the nonwoven fabric portion of topsheet 28 prior to use. A suitable material commonly used to pigment polymers is titanium dioxide. Titanium dioxide will provide the fluid impervious areas with a white pigmentation that blends well with the nonwoven fabric portion of the topsheet 28.

Preferably, the fluid impervious areas 36 on topsheet 28 cover from about 10 percent to about 70 percent of the area of topsheet 28, and more preferably, the fluid impervious areas 36 on topsheet 28 cover from about 20 percent to about 40 percent of the area of topsheet 28.

Preferably, the ink or other material comprising the fluid impervious areas 36 is applied to the nonwoven topsheet 28 by using a silk screen printing process. This particular process is well known in the field of printing and involves squeezing a viscous liquid through a patterned screen. Once printed on nonwoven topsheet 28, fluid impervious areas 36 are dried by placing the topsheet 28 in an oven.

Another method of applying fluid impervious areas 36 to nonwoven topsheet 28 is by using a gravure printing process. The gravure printing process uses a drum having a pattern of depressions located thereon. The depressions on the drum are filled with a material which will eventually form the fluid impervious areas 36 on the nonwoven topsheet 28. The material is deposited onto the topsheet substrate when the drum is brought into contact with the substrate. This method is more appropriate with materials which are printed at elevated temperatures and then cooled to solidify.

Figure 5:
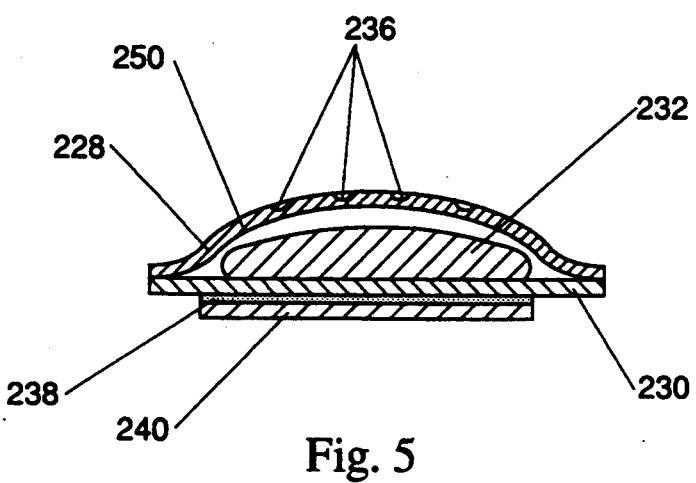
FIG. 5 is a cross-sectional view of a topsheet of the present invention depicting the fluid impervious areas as depressed zones.

In a preferred embodiment seen in FIG. 5, fluid impervious areas 236 are preferably spaced sufficiently apart so that the wearer's skin when placed in contact with the first or wearer contacting surface 228a of sanitary napkin 220 will have sufficient contact with nonwoven fibers 250 of topsheet 228. Furthermore, fluid impervious areas 236 should be at or below the uppermost plane of the fibers 250 of which the topsheet 228 is comprised, thereby allowing the wearer to experience the soft, tactile feel of the nonwoven material.

In the embodiment depicted in FIG. 5, prior to use the fluid impervious areas 236 provide the user with a subtly perceived visual pattern as the fluid impervious areas 236 have little or no visual contrast with the fibers 250 of the nonwoven fabric portion of topsheet 228. Both prior to and during use the absorbent article 220, as depicted in FIG. 5, allows the fiber based nonwoven portion of topsheet 228 to be perceived tactilely by the user. After use, that is after bodily fluids have been deposited on the topsheet 228, the fluid impervious areas 236 provide the user with a visually clean and dry surface as the fluid impervious areas 236 contrast visually with the wetted fibers 250 of the nonwoven fabric portion of topsheet 228.

Figure 4:
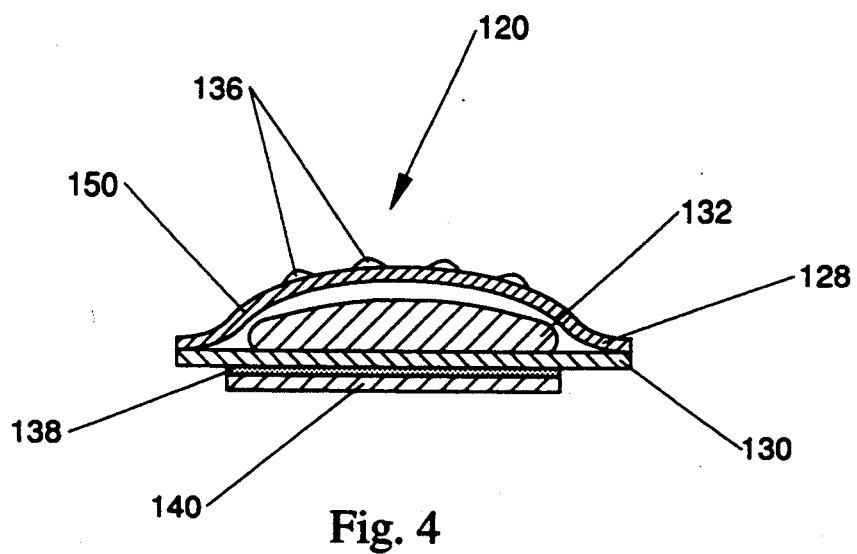
FIG. 4 is a cross-sectional view of a topsheet of the present invention depicting the fluid impervious areas as raised zones.

Another preferred embodiment is depicted in FIG. 4. In this embodiment of the present invention the fluid impervious areas 136 are raised slightly above the uppermost plane of the fibers 150 of which the topsheet 128 is comprised. The visually perceived impression by the user of the sanitary napkin 120 is similar if not the same as that of the embodiment of the sanitary napkin 220 as depicted in FIG. 5. However, in this embodiment, the user experiences the tactile impression provided by the fluid impervious areas 136 both prior to and during use. The advantage to the tactile impression provided by the fluid impervious areas 136 is that during use the first or wearer contacting surface 120a of the pad 120 feels clean and dry, since less menses remains on the fluid impervious areas 136 than in fibers 150 of the nonwoven portion of topsheet 128.

In addition, in preferred embodiments of the present invention, at least the fluid pervious portion, i.e., the nonwoven fabric portion, of the topsheet 28 can be treated with a surfactant. This can be accomplished with any of the common techniques well known to those skilled in the art. Suitable methods for treating the topsheet with a surfactant are described in a number of references including U.S. Pat. Nos. 4,950,264 issued to Osborne on Aug. 21, 1990 and 5,009,563 issued to Osborne on Apr. 23, 1991 and hereby being incorporated herein by reference.

If a surfactant treatment is desired, it should be noted that the surfactant should be limited to the nonwoven fibers of topsheet 28, 128 or 228. To ensure a clean and dry surface impression the fluid impervious areas 36, 136 and 236 should remain somewhat mensesphobic so that menses does not "wet out" and remain on the fluid impervious areas.

Treating the topsheet 28 with a surfactant renders the surface of the topsheet 28 more hydrophilic. This results in fluid penetrating topsheet 28 faster than it would have if the surface were not treated. This diminishes the likelihood that menstrual fluids will flow off topsheet 28, 128, or 228 rather than being absorbed by the absorbent core 32.

B. The Absorbent Core

The absorbent core 32 is positioned between the topsheet 28 and the backsheet 30. The absorbent core 32 provides the means for absorbing menstrual fluid and other bodily exudates. The absorbent core 32 need not have an absorbent capacity much greater than the total amount of exudates anticipated to be absorbed. The absorbent core 32 is generally compressible, conformable, and non-irritating to the user's skin.

The absorbent core 32 can comprise any material used in the art for such purpose. Examples include natural materials such as cotton, comminuted wood pulp which is generally referred to as airfelt, creped cellulose wadding, peat moss, cross-linked cellulose fibers, absorbent foams, absorbent sponges, synthetic staple fibers, polymeric fibers, hydrogel-forming polymer gelling agents, or any equivalent material or combinations of materials.

Suitable cross-linked cellulose fibers are described in U.S. Pat. No. 4,888,093, issued to Cook, et al. on Dec. 19, 1989; U.S. Pat. No. 4,822,543, issued to Dean, et al. on Apr. 18, 1989; U.S. Pat. No. 4,889,595, issued to Schoggen, et al. on Dec. 26, 1989; U.S. Pat. No. 4,889,596, issued to Schoggen, et al. on Dec. 26, 1989; U.S. Pat. No. 4,898,642, issued to Moore, et al. on Feb. 6, 1990; and U.S. Pat. No. 4,935,022, issued to Lash, et al. on Jun. 19, 1990, all of said patents being hereby incorporated herein by reference.

The characteristics of the absorbent core 32 for particular types of absorbent articles are described in greater detail in the patents and documents incorporated by reference herein, and the patents and other documents incorporated by reference in those documents, the disclosures of which are all incorporated by reference herein. Other suitable absorbent core arrangements are described in U.S. Pat. Nos. 4,988,344 issued to Reising, et al. on Jan. 29, 1991 and 4,988,345 issued to Reising on Jan. 29, 1991, which are also hereby incorporated herein by reference herein. Other possible core 32 materials are described in U.S. Pat. No. 4,475,911 issued to Gellert on Oct. 9, 1984 and being hereby incorporated herein by reference.

The absorbent article 20 could also include any additional layers or other components such as are described in the patents incorporated by reference. For example, the absorbent article 20 may comprise an acquisition layer or patch of cross-linked cellulose fibers positioned between the topsheet 28 and the absorbent core 32.

C. The Backsheet

The backsheet 30 is impervious to fluids and is preferably manufactured from a thin plastic film, although other flexible liquid impervious materials may also be used. The backsheet 30 prevents liquid contained in absorbent core 32 from wetting articles which contact the absorbent article 20. Polyethylene films having a thickness of from about 0.001 to about 0.002 inches (0.0025 to 0.0051 cm.) have been used for the backsheet 30 with satisfactory results. As used herein, the term "flexible" refers to materials which are compliant and which will readily conform to the general shape and contours of the human body.

The backsheet 30 is superimposed on the garment-facing side 32b of absorbent core 32 and preferably extends beyond the edges thereof. The topsheet 28 is superimposed over the body-facing side 32a of the absorbent core 32 and may also extend beyond the edges of the core 32. The absorbent core 32 is, therefore, positioned between the topsheet 28 and the backsheet 30. The topsheet 28 and backsheet 30 are joined to each other such as around their peripheries. The topsheet 28 and backsheet 30 can be joined in any suitable manner such as by the use of adhesives, crimping, heat-sealing, or ultrasonic bonding.

FIGS. 2 and 3 also show the fasteners, such as adhesive fastening means 38, which are adapted to secure the sanitary napkin 20 to the crotch region of an undergarment. Suitable adhesive fasteners are described in greater detail in U.S. Pat. No. 4,917,697 issued to De Jonckheere on Apr. 17, 1990 and hereby incorporated herein by reference. The fasteners used with the present invention are not limited to adhesive attachment means. Any type of fastener used in the art can be used for such purpose. For example, the sanitary napkin 20 could be secured to the wearer's undergarment by the fastener described in U.S. Pat. No. 4,946,527 issued to Battrell on Aug. 7, 1990 and hereby incorporated herein by reference.

The adhesive fastening means 38 is covered by removable release liner, designated 40. The pressure-sensitive adhesives should be covered with release liners 40 to keep the adhesives from sticking to extraneous surfaces prior to use. Suitable release liners are described in U.S. Pat. No. 4,917,697. A suitable wrapper that both serves as a package for a sanitary napkin and as a cover for adhesives on the same is described in U.S. Pat. No. 4,556,146 issued to Swanson, et al. on Dec. 3, 1985 and hereby incorporated herein by reference.

III. The Absorbent Article

The present invention provides an absorbent article having the visual appearance and tactile impression of a fiber based nonwoven topsheet prior to use and the clean and dry appearance of a film based topsheet after use. Thus, the present invention satisfies the two major groups of users who prefer both of these important characteristics. The tactile impression may be tailored to fit the needs and/or wants of the users by varying the penetration of the fluid impervious areas into the fiber based nonwoven topsheet.

Prior to use, the user feels the fibrous texture of the fiber based nonwoven portion of the topsheet. As bodily fluid is deposited on the topsheet of the absorbent article, it wets the fluid pervious nonwoven fabric portion of the topsheet. The wetted fluid pervious nonwoven fabric portion of the topsheet contrasts visually with the fluid impervious areas of the topsheet, creating the perception of a clean and dry topsheet.

While particular embodiments of the present invention have been illustrated and described, it will be obvious to those skilled in the art that various changes and modifications can be made without departing from the spirit and scope of the invention, and it is intended to cover in the appended claims all such modifications that are within the scope of this invention.

What is claimed is:

1. An absorbent article comprising:
   (a) a fluid pervious topsheet, said topsheet including a bonded fluid pervious nonwoven material having a first surface, said first surface of said nonwoven material having a patterned network of mensophobic fluid impervious areas deposited thereon which extend above said first surface of said nonwoven material, such that bodily fluid deposited on said topsheet is transported through said fluid pervious nonwoven material thereby wetting said fluid pervious nonwoven material, said wetted fluid pervious nonwoven material contrasting visually with said mensophobic fluid impervious areas;
   (b) a fluid impervious backsheet joined to said topsheet; and
   (c) an absorbent core positioned between said topsheet and said backsheet.

2. The absorbent article of claim 1, wherein said mensophobic fluid impervious areas are pigmented.

3. The absorbent article of claim 1, wherein said nonwoven material is a carded material.

4. The absorbent article of claim 1, wherein said nonwoven material is a spunbonded material.

5. The absorbent article of claim 1, wherein said mensophobic fluid impervious areas are cellulose acetate.

6. The absorbent article of claim 1, including an adhesive fastening means secured to said backsheet adapted to secure said absorbent article to an undergarment.

7. The absorbent article of claim 1, wherein said absorbent article is a disposable sanitary napkin.

8. The absorbent article of claim 1, wherein said absorbent article is a disposable diaper.

9. The absorbent article of claim 1, wherein said nonwoven material is apertured.

10. The absorbent article of claim 9, wherein said mensophobic fluid impervious areas cover from about 10 percent to about 70 percent of said first surface of said topsheet.

11. An absorbent article comprising:
   (a) a fluid pervious topsheet, said topsheet including a bonded fluid pervious apertured nonwoven material having a first surface, said first surface of said apertured nonwoven material having a patterned network of mensophobic fluid impervious areas deposited thereon which extend above said first surface of said nonwoven material, such that bodily fluid deposited on said topsheet is transported through said fluid pervious apertured nonwoven material thereby wetting said fluid pervious apertured nonwoven material, said wetted fluid pervious apertured nonwoven material contrasting visually with said mensophobic fluid impervious areas;
   (b) a fluid impervious backsheet joined to said topsheet; and
   (c) an absorbent core positioned between said topsheet and said backsheet.

12. The absorbent article of claim 11, wherein said mensophobic fluid impervious areas are pigmented.

13. The absorbent article of claim 11, wherein said apertured nonwoven material is hydroapertured.

14. The absorbent article of claim 11, wherein said absorbent article is a disposable sanitary napkin.

15. The absorbent article of claim 11, wherein said absorbent article is a disposable diaper.

16. An absorbent article comprising:
   (a) a fluid pervious topsheet, said topsheet including a bonded fluid pervious nonwoven material having a first surface with a predetermined area, said first surface of said nonwoven material having a patterned network of mensophobic fluid impervious areas deposited thereon which extend above said first surface of said nonwoven material, said mensophobic fluid impervious areas covering from about 10 percent to about 70 percent of said first surface area, such that bodily fluid deposited on said topsheet is transported through said fluid pervious nonwoven material thereby wetting said fluid pervious nonwoven material, said wetted fluid pervious nonwoven material contrasting visually with said mensophobic fluid impervious areas;
   (b) a fluid impervious backsheet joined to said topsheet; and
   (c) an absorbent core positioned between said topsheet and said backsheet.

17. The absorbent article of claim 16, wherein said mensophobic fluid impervious areas are pigmented.

18. The absorbent article of claim 16, wherein said nonwoven material is apertured.

19. The absorbent article of claim 16, wherein said absorbent article is a disposable sanitary napkin.

20. The absorbent article of claim 16, wherein said absorbent article is a disposable diaper.

* * * * *